(12) United States Patent
Bristow (10) Patent No.: US 10,059,676 B2
(45) Date of Patent: *Aug. 28, 2018

(54) PROCESS FOR PREPARING A NOVEL CRYSTALLINE FORM OF IODOSULFURON-METHYL-SODIUM AND USE OF THE SAME

(71) Applicant: ROTAM AGROCHEM INTERNATIONAL COMPANY LIMITED, Chai Wan (HK)

(72) Inventor: James Timothy Bristow, Chai Wan (HK)

(73) Assignee: ROTAM AGROCHEM INTERNATIONAL COMPANY LIMITED, Chai Wan (HK)

( * ) Notice: Subject to any disclaimer, the term of this patent is extended or adjusted under 35 U.S.C. 154(b) by 91 days.

This patent is subject to a terminal disclaimer.

(21) Appl. No.: 14/926,133

(22) Filed: Oct. 29, 2015

(65) Prior Publication Data

US 2017/0121294 A1 May 4, 2017

(51) Int. Cl.
*C07D 251/42* (2006.01)
*A01N 47/36* (2006.01)

(52) U.S. Cl.
CPC .......... *C07D 251/42* (2013.01); *A01N 47/36* (2013.01)

(58) Field of Classification Search
None
See application file for complete search history.

(56) References Cited

U.S. PATENT DOCUMENTS

| 5,463,081 A | 10/1995 | Ort et al. |
| 5,688,745 A * | 11/1997 | Ort .......................... A01N 47/36 504/231 |
| 2011/0237436 A1* | 9/2011 | Olenik .................... A01N 25/12 504/231 |

OTHER PUBLICATIONS

Vippagunta et al., Crystallline Solids, Advance Drug Delivery Reviews (2001), vol. 48, pp. 3-26.*
Crystallization—Science and Technology (2012), pp. 183-204.*
Monograph (2000), Iodosulfuron-methyl-sodium.*

* cited by examiner

*Primary Examiner* — Hasan Syed Ahmed
*Assistant Examiner* — Frank Choi
(74) *Attorney, Agent, or Firm* — Dickinson Wright PLLC (57) ABSTRACT

A crystalline form of iodosulfuron-methyl-sodium of formula (I), the crystal preparation process, the analyses of the crystal through various analytical methods and using the crystal to prepare stable agrochemical formulation. The invention also describes the use of various solvents towards the crystalline form preparation conditions.

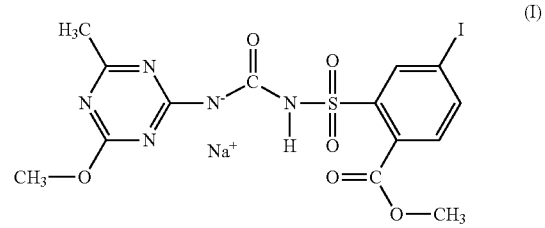

10 Claims, 3 Drawing Sheets

PROCESS FOR PREPARING A NOVEL CRYSTALLINE FORM OF IODOSULFURON-METHYL-SODIUM AND USE OF THE SAME

BACKGROUND

Field

The present disclosure relates to a crystalline form of sodium salt of methyl 4-iodo-2-[[[[(4-methoxy-6-methyl-1,3,5-triazin-2-yl)amino]carbonyl]amino] sulfonyl]benzoate (iodosulfuron-methyl-sodium), to its preparation processes and to its use in agrochemical preparations.

Description of Related Art

The sodium salt of methyl 4-iodo-2-[[[[(4-methoxy-6-methyl-1,3,5-triazin-2-yl)amino] carbonyl]amino]sulfonyl] benzoate (iodosulfuron-methyl-sodium) is a potent herbicide having high selectivity, high efficiency, low toxicity and other desirable attributes. Iodosulfuron-methyl-sodium has molecular formula of $C_{14}H_{13}IN_5NaO_6S_1$. Its chemical structure is:

(I)

It is used post-emergence on crops, such as wheat and cereals, against a variety of annual and perennial grasses and broadleaved weeds. It is rather less toxic towards algae and is of generally low toxicity towards most wildlife.

The commercially available iodosulfuron-methyl-sodium, which is usually manufactured by the process described in U.S. Pat. No. 5,463,081, is present in an amorphous state. It has been found that iodosulfuron-methyl-sodium in the amorphous state is highly unstable. It will generally undergo significant hydrolysis when dissolved or dispersed in water. Furthermore, hydrolysis can occur during storage, particularly where the compound is exposed to moisture. As a result, the stability of iodosulfuron-methyl-sodium is of great concern with respect to providing commercially available formulations. Therefore, there is a need to provide a novel form of iodosulfuron-methyl-sodium with increased stability in formulations.

SUMMARY

Accordingly, an embodiment of the invention provides a novel crystalline form of iodosulfuron-methyl-sodium, termed "crystalline modification I", and a process for its preparation, as well as agrochemical compositions containing it, and methods for using it in agrochemical applications, such as methods for applying it to plants, plant loci, and plant parts. The novel crystalline modification I has been found to have increased stability relative to the amorphous form. Accordingly, an embodiment of the invention also provides compositions for controlling undesirable plant growth, such as weeds, comprising the crystalline modification I of iodosulfuron-methyl-sodium on its own, as a mixture with auxiliaries and carriers, and as a mixture with other active compounds. The use of the crystalline modification I of iodosulfuron-methyl-sodium in the control of undesired plant growth and a method for the same are also provided by an embodiment of the invention.

BRIEF DESCRIPTION OF DRAWINGS

Various features and aspects of the embodiments of the invention disclosed herein can be more clearly understood by reference to the drawings, which are intended to exemplify and illustrate, but not to limit, the scope of the invention, and wherein.

DETAILED DESCRIPTION OF SPECIFIC EMBODIMENTS

The invention can be more clearly understood by reference to the following detailed description of specific embodiments thereof, which is intended to illustrate, but not limit, the scope of the appended claims.

It has been found that the embodiment of crystalline modification I of iodosulfuron-methyl-sodium has a significant increase in its stability, which significantly reduces or avoids the hydrolysis problems encountered in current commercially available formulations, which contain the amorphous form of iodosulfuron-methyl-sodium. In addition, it has been found that the crystalline modification I of iodosulfuron-methyl-sodium is easier to comminute or grind into particles, compared to amorphous iodosulfuron-methyl-sodium prepared in accordance with the disclosure of U.S. Pat. No. 5,463,081. This allows the preparation of commercial formulations such as suspension concentrates (SC), oil-based suspension concentrates (OD), water-dispersible granules (WG) and water-soluble granules (SG). Hence, it is possible to prepare any formulation of iodosulfuron-methyl-sodium in crystalline modification I, as will be disclosed hereinafter.

By virtue of its high stability, the crystalline modification I of iodosulfuron-methyl-sodium disclosed herein is highly suitable for preparing compositions for controlling undesirable weeds.

According to a first aspect of the invention a crystalline modification I of iodosulfuron-methyl-sodium is provided, exhibiting at least 3 of the following reflexes as 2θ values in an X-ray powder diffractogram recorded using Cu-Kα radiation at 25° C.:

| | |
|---|---|
| 2θ=11.558±0.2 | (1) |
| 2θ=14.569±0.2 | (2) |
| 2θ=18.045±0.2 | (3) |
| 2θ=19.442±0.2 | (4) |
| 2θ=20.633±0.2 | (5) |
| 2θ=23.226±0.2 | (6) |
| 2θ=26.145±0.2 | (7) |
| 2θ=27.199±0.2 | (8) |

$$2\theta=27.877\pm0.2 \quad (9)$$

$$2\theta=29.090\pm0.2 \quad (10)$$

Figure 2:
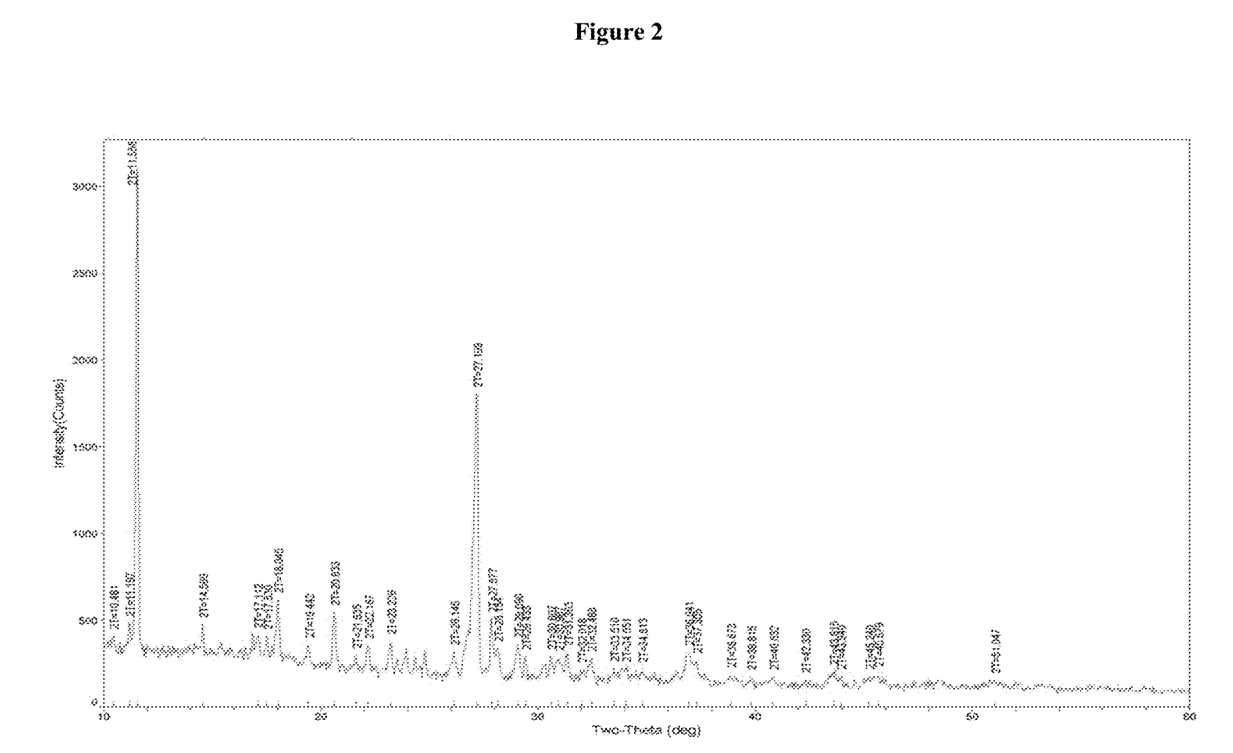
FIG. 2 is a graph showing the results of a powder X-ray diffractogram of an embodiment of crystalline modification I of iodosulfuron-methyl-sodium.

The crystalline modification I of an embodiment of iodosulfuron-methyl-sodium of the invention is characterized by an X-ray powder diffractogram having at least three of the reflexes indicated above. Preferably, the crystalline modification I is one having at least four of the aforementioned reflexes, more preferably at least five, six or seven, or eight of said reflexes. The crystalline modification I of an embodiment of iodosulfuron-methyl-sodium can contain 3 or more of the reflexes indicated above in any combination of reflexes. For example, the crystalline modification I of an embodiment of iodosulfuron-methyl-sodium can contain at least reflexes (1), (2), and (3), or at least reflexes (2), (3), and (4), or reflexes (1), (3), and (4), or any other combination of at least three reflexes. An X-ray powder diffractogram of an embodiment of the crystalline modification I of iodosulfuron-methyl-sodium is shown in FIG. 2, which will be described in detail hereinafter.

According to a preferred embodiment the crystalline form A exhibits at least 3, 4, or 5 or all of the reflexes from the following, again in any combination thereof:

$$2\theta=11.558\pm0.2 \quad (1)$$

$$2\theta=14.569\pm0.2 \quad (2)$$

$$2\theta=18.045\pm0.2 \quad (3)$$

$$2\theta=20.633\pm0.2 \quad (5)$$

$$2\theta=23.226\pm0.2 \quad (6)$$

$$2\theta=27.199\pm0.2 \quad (8)$$

The crystalline modification I of iodosulfuron-methyl-sodium according to an embodiment of the invention may be further characterized by Infrared (IR) spectroscopy. The IR spectrum of an embodiment of the crystalline modification I is showed in FIG. 1 with characteristic bands at one or more of 3516.78, 3330.55, 2946.18 and 2160.93 $cm^{-1}$.

All IR spectra were obtained using the following acquisition parameters:

| | |
|---|---|
| FT-IR spectrometer | Bruker Tensor37 |
| Diamond ATR unit | from Specac |
| Wavelength range | 550-4000 $cm^{-1}$ |
| Resolution | 4 $cm^{-1}$ |
| Number of scans | 16 |

Methods for preparing amorphous iodosulfuron-methyl-sodium are well known in the art. Amorphous iodosulfuron-methyl-sodium is manufactured and available on a commercial scale. A particularly suitable method for preparing amorphous iodosulfuron-methyl-sodium is described in U.S. Pat. No. 5,463,081.

According to an embodiment of the invention, the crystalline modification I of iodosulfuron-methyl-sodium can be obtained by the processes below:

Iodosulfuron-methyl-sodium in amorphous state is dissolved and then crystallized from solvents.

In one aspect, the invention provides a process for preparing a crystalline modification I of iodosulfuron-methyl-sodium comprising steps of:

i) preparing a solution of an amorphous iodosulfuron-methyl-sodium in a solvent;
ii) effecting crystallization of iodosulfuron-methyl-sodium from the solution to obtain a solid precipitate; and
iii) isolating the solid precipitate.

Suitable solvents for preparing iodosulfuron-methyl-sodium crystalline modification I include halogenated hydrocarbons (for example, chlorobenzene, bromobenzene, dichlorobenzene, chlorotoluene and trichlorobenzene), ethers (for example, ethyl propyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether, methyl-tetrahydrofuran, polyethers of ethylene oxide and/or propylene oxide), nitrated hydrocarbons (for example, nitromethane, nitroethane, nitropropane, nitrobenzene, chloronitrobenzene and o-nitrotoluene), aliphatic, cycloaliphatic or aromatic hydrocarbons (for example, pentane, n-hexane, n-heptane, n-octane, nonane), cymene, petroleum fractions within a boiling range of from 70° C. to 190° C., cyclohexane, methylcyclohexane, petroleum ether, ligroin, octane, benzene, toluene and xylene), esters (for example, malonates, acetic acid n-butyl ester (n-butyl acetate), methyl acetate, ethyl acetate, isobutyl acetate, dimethyl carbonate, diethyl carbonate, dibutyl carbonate and ethylene carbonate), and aliphatic alcohols (for example, methanol, ethanol, n-propanol, isopropanol, n-butanol and tert-amyl alcohol), and mixtures of any of these.

Preferred solvents include ethers, aromatic hydrocarbons (such as benzene, toluene, xylene, chlorobenzene), esters and aliphatic alcohols and mixtures thereof. Particularly preferred solvents or solvent mixtures include isopropanol, toluene, methyl-tetrahydrofuran, diethyl carbonate, chlorobenzene, n-butyl acetate, isobutyl acetate, n-butanol, methanol, ethanol, ethyl malonate, methyl t-butyl ether, and mixtures of these, particularly mixtures of toluene and butanol, mixtures of toluene and n-butyl acetate, mixtures of ethyl malonate and methyl t-butyl ether, as well as mixtures of butyl acetate and methyl t-butyl ether. Solvent mixtures of more than 2 or 3 or 4 components are also envisaged by the invention.

In a particular embodiment of the invention, it is preferred that the solvent is or includes an alcohol.

Hence, according to a preferred embodiment in step (i), amorphous iodosulfuron-methyl-sodium is dissolved in a solvent comprising an alcohol. More preferably, the amorphous iodosulfuron-methyl-sodium is dissolved in a solvent comprising methanol and/or ethanol (including mixtures thereof).

In step (ii), iodosulfuron-methyl-sodium is crystallized from the solution. Techniques for effecting crystallization of iodosulfuron-methyl-sodium from the solution are known to those skilled in the art. For example, in an embodiment where the solution in step (i) is formed at elevated temperatures, crystallization may be effected by cooling the solution to room or ambient temperature. In one preferred embodiment, crystallization is effected by concentrating the solution formed in step (i) of the process. Alternatively, or in addition thereto, seed crystals, in particular seed crystals of the aforementioned crystalline modification I of iodosulfuron-methyl-sodium, may be added to the solution formed in step (i), to facilitate and/or enhance crystallization.

It is preferred that the solid precipitate of iodosulfuron-methyl-sodium recovered during the crystallization stage is washed with a solvent for one or more times. Preferably, the solvent employed in the washing stage consists of one or more components of the solvent employed for forming the solution in step (i), as described hereinbefore. Methanol and/or ethanol (including mixtures thereof) are particularly suitable solvents for washing the recovered solid of iodosulfuron-methyl-sodium.

The invention, in an embodiment, also relates to a composition comprising the crystalline modification I of iodosulfuron-methyl-sodium. The amount of the crystalline modification I of iodosulfuron-methyl-sodium is desirably less than 75% by weight of the composition, preferably less than 50% by weight of the composition, more preferably less than 30% by weight of the composition, still more preferably about 25% by weight of the composition.

The use of iodosulfuron-methyl-sodium, in the amorphous form, as a herbicide is known in the art and is used on a commercial scale. The crystalline modification I of iodosulfuron-methyl-sodium is also active in controlling weeds. Techniques of formulating and applying iodosulfuron-methyl-sodium in the crystalline modification I are analogous to those known in the art for the amorphous form, for example as disclosed in the prior art documents disclosed hereinbefore. Iodosulfuron-methyl-sodium in the crystalline modification I of the present invention may be formulated and applied in an analogous manner to those disclosed in these documents for the amorphous form of iodosulfuron-methyl-sodium.

Accordingly, in a further aspect, the invention provides a herbicidal composition comprising iodosulfuron-methyl-sodium in the crystalline modification I as defined hereinbefore.

Accordingly, the invention furthermore provides processes for preparing compositions for controlling weeds using the crystalline modification I of iodosulfuron-methyl-sodium.

Accordingly, the invention also provides a method of controlling unwanted plant growth comprising applying to a plant, plant part, or locus thereof a herbicidally effective amount of crystalline modification I of iodosulfuron-methyl-sodium according to claim 1

The crystalline modification I of iodosulfuron-methyl-sodium can be incorporated in a known manner to the customary formulations, such as suspension concentrates (SC), oil-based suspension concentrates (OD), water-soluble granules (SG), dispersible concentrates (DC), emulsifiable concentrates (EC), emulsion seed dressings, suspension seed dressings, granules (GR), microgranules (MG), suspoemulsions (SE) and water-dispersible granules (WG) using suitable herbicidally acceptable auxiliaries, carriers and solvents.

In this context, the crystalline modification I of iodosulfuron-methyl-sodium may be present in a concentration sufficient to achieve the required or desired dosage, e.g., in a concentration of from about 0.1 to about 50% by weight of the total mixture. The formulations are prepared, for example, by extending the crystalline modification I of iodosulfuron-methyl-sodium with water, solvents and carriers, using, if appropriate, emulsifiers and/or dispersants, and/or other auxiliaries.

These formulations are prepared in a known manner by mixing the crystalline modification I of iodosulfuron-methyl-sodium with one or more herbicidally acceptable auxiliaries, for example, liquid diluents, solid diluents, wetting agents, dispersants, thickening agents and other formulation ingredients.

Liquid diluents include, but are not limited to, water, N, N-dimethylamide, dimethyl sulfoxide, N-alkylpyrrolidone, ethylene glycol, polypropylene glycol, propylene carbonate, dibasic esters, paraffines, alkylbenzenes, alkyl naphthalenes, glycerine, triacetine, oils of olive, castor, linseed, sesame, corn, peanut, cotton-seed, soybean, rape-seed and coconut, ketones such as cyclohexanone, 2-heptanone, isophorone and 4-hydroxy-4-methyl-2-pentanone, acetates such as hexyl acetate, heptyl acetate and octyl acetate, and alcohols such methanol, cyclohexanol, decanol, benzyl and tetrahydrofurfuryl alcohol, and mixtures thereof.

Solid diluents can be water-soluble or water-insoluble. Water-soluble solid diluents include, but are not limited to, salts such as alkali metal phosphates (e.g., sodium dihydrogen phosphate), alkaline earth phosphates, sulfates of sodium, potassium, magnesium and zinc, sodium and potassium chloride, sodium acetate, sodium carbonate and sodium benzoate, and sugars and sugar derivatives such as sorbitol, lactose, sucrose and mannitol, and mixtures thereof. Examples of water-insoluble solid diluents include, but are not limited to clays, synthetic and diatomaceous silicas, calcium and magnesium silicates, titanium dioxide, aluminum, calcium and zinc oxides, and mixtures thereof.

Wetting agents include, but are not limited to, alkyl sulfosuccinates, laureates, alkyl sulfates, phosphate esters, acetylenic diols, ethoxyfluornated alcohols, ethoxylated silicones, alkyl phenol ethyoxylates, benzene sulfonates, alkyl-substituted benzene sulfonates, alkyl a-olefin sulfonates, naphthalene sulfonates, alkyl-substituted naphthalene sulfonates, condensates of naphthalene sulfonates and alkyl-substituted naphthalene sulfonates with formaldehyde, and alcohol ethoxylates, and mixtures thereof. Alkyl naphthalene sulphonates, sodium salts are particularly useful for the composition of the invention.

Dispersants include, but are not limited to, sodium, calcium and ammonium salts of ligninsulfonates (optionally polyethoxylated); sodium and ammonium salts of maleic anhydride copolymers; sodium salts of condensed phenolsulfonic acid; and naphthalene sulfonate-formaldehyde condensates. Ligninsulfonates such as sodium ligninsulfonates are particularly useful for the composition of the invention. Naphthalene sulfonate-formaldehyde condensates such as naphthalenesulfonic acid, polymers with formaldehyde, and sodium salts are particularly useful for the composition of the invention Thickening agents include, but are not limited to, guar gum, pectin, casein, carrageenan, xanthan gum, alginates, methylcellulose, hydroxyethylcellulose, hydroxypropylcellulose, and carboxymethylcellulose, and mixtures thereof. Synthetic thickeners include derivatives of the former categories, and also polyvinyl alcohols, polyacrylamides, polyvinylpyrrolidones, various polyethers, their copolymers as well as polyacrylic acids and their salts, and mixtures thereof. Alkylpolyvinylpyrrolidones are particularly useful for the composition of the invention Other formulation ingredients can also be used in the present invention such as dyes, defoamers, drying agents, and the like. These ingredients are known to one skilled in the art.

The crystalline modification I of iodosulfuron-methyl-sodium according to an embodiment of the invention can be present in formulations and in its use forms, prepared from these formulations, and as a mixture with other active compounds (such as insecticides, attractants, sterilizing agents, bactericides, acaricides, nematicides, fungicides, growth-regulating substances, herbicides, safeners, fertilizers and semiochemicals) or with agents for improving plant properties. Other active compounds include sulfonylurea herbicides, triazole herbicides, benzoylcyclohexanedione herbicides.

All plants and plant parts can be treated in accordance with the present invention. In the present context, plants are to be understood as meaning all plants and plant populations such as desired and undesired wild plants or crop plants (including naturally occurring crop plants). Crop plants can be plants which can be obtained by conventional breeding and optimization methods, by biotechnological and genetic engineering methods, or by combinations of these methods, including the transgenic plants and the plant cultivars which can or cannot be protected by plant breeders' rights. Plant parts are to be understood as meaning all parts and organs of plants above and below the ground, such as shoot, leaves, needles, stalks, stems, flowers, fruit bodies, fruits, seeds, roots, tubers and rhizomes. Harvested materials, and vegetative and generative propagation materials, for example, cutting, tubers, meristem tissue, rhizomes, offsets, seeds, single and multiple plant cells and any other plant tissues, are also included.

As used herein, the term "about," when used in connection with a numerical amount or range, means somewhat more or somewhat less than the stated numerical amount or range, to a deviation of ±10% of the stated numerical amount or endpoint of the range.

"Surrounding," as used herein, refers to the place on which the plants are growing, the place on which the plant propagation materials of the plants are sown or the place on which the plant propagation materials of the plants will be sown.

The term "herbicidally effective amount" as used herein, refers to the quantity of such a compound or combination of such compounds that is capable of producing a controlling effect on the growth of plants. The controlling effects include all deviation from the natural development of the target plants, for example killing, retardation of one or more aspects of the development and growth of the plant, leaf burn, albinism, dwarfing and the like.

Treatment of the plants and plant parts with the compositions or formulations of the inventions according to the invention is carried out directly or by allowing the compositions or formulations to act on their surroundings, habitat or storage space by the customary treatment methods. Examples of these customary treatment methods include dipping, spraying, vaporizing, fogging, broadcasting, painting on in the case of propagation material, and applying one or more coats particularly in the case of seed.

The compositions or formulations of the present invention may be used to control dicotyledonous weeds, such as *Galium*, *Viola*, *Veronica*, *Lamium*, *Stellaria*, *Amaranthus*, *Sinapis*, *Ipomoea*, *Matricaria*, *Abutilon*, *Sida*, *Convolvulus*, *Cirsium*, *Rumex* and *Artemisia*.

The compositions or formulations of the present invention may also be used to control monocotyledonous weeds, such as *Avena*, *Lolium*, *Alopecurus*, *Phalaris*, *Echinochloa*, *Digitaria*, *Setaria*, *Cyperus* spp., *Agropyron*, *Cynodon*, *Imperata* and *Sorghum*.

The benefits of the present invention are seen most when the herbicidal composition is applied to kill weeds in growing crops of useful plants: such as maize (corn) including field corns, pop corns and sweet corns, cotton, wheat, barley, rye, triticale, rice, oats, potatoes, sugar beets, plantation crops (such as bananas, fruit trees, rubber trees, tree nurseries), vines, asparagus, bushberries (such as blueberries), caneberries, cranberries, flax, grain sorghum, okra, peppermint, rhubarb, spearmint and sugarcane. In this invention, wheat, barley, rye, triticale are particularly suitable crops for treatment of weeds by the presently disclosed crystalline modification.

All percentages are given in weight % unless otherwise indicated.

Embodiments of the invention will now be described by way of the following examples which are provided for illustrative purposes only, and not intended to limit the scope of the disclosure or the appended claims.

EXAMPLES

Example 1

Preparation of Amorphous Iodosulfuron-methyl-sodium in accordance with the disclosure of U.S. Pat. No. 5,463,081

Methyl 2-Amino-4-Iodobenzoate (Example 3 in U.S. Pat. No. 5,463,081)

A solution of 16.1 g of 2-acetylamino-4-iodobenzoic acid (m.p. 233° C.-235° C.; synthesized in accordance with U.S. Pat. No. 4,762,838) in 325 ml of absolute methanol is saturated at 0° C. with dry hydrogen chloride gas. The mixture is heated to the boil for 15 hours, cooled to room temperature, resaturated using dry hydrogen chloride gas, and allowed to stand at room temperature for 24 hours. The solvent is evaporated in vacuo, the residue is taken up in dichloromethane, and the organic phase is washed with a saturated aqueous sodium hydrogen carbonate solution until free from acid. The organic phase is dried over $Na_2SO_4$, and evaporated in vacuo. This gives 13.8 g of methyl 2-amino-4-iodobenzoate of m.p. 63° C.-67° C.

Bis (2-methoxycarbonyl-5-iodobenzene)disulfide (Example 4 in U.S. Pat. No. 5,463,081)

13.8 g of methyl 2-amino-4-iodobenzoate are treated with 48 ml of glacial acetic acid and subsequently with 86 ml of concentrated hydrochloric acid. A solution of 3.8 g of sodium nitrite in 15 ml of water is slowly added dropwise to this suspension which is cooled to −5° C., and stirring is continued at this temperature for 30 minutes. This cooled diazonium salt solution is added dropwise at 0° C. to a solution of 20 ml of sulfur dioxide, 60 ml of glacial acetic acid, 10 ml of water and 3.1 g of copper(II) chloride dihydrate, and stirring is continued first for 1 hour at 0° C. and then overnight at room temperature. The reaction mixture is poured into 1 l of ice-water, and the product is filtered off with suction. This gives 12.7 g of bis(2-methoxycarbonyl-5-iodobenzene)disulfide of m.p. 133° C.-135° C.

2-Methoxycarbonyl-5-iodobenzenesulfochloride (Example 5 in U.S. Pat. No. 5,463,081)

Chlorine gas is passed at 20° C.-25° C. into 12.2 g of bis(2-methoxycarbonyl-5-iodobenzene)disulfide in a solution of 30 ml of 1,2-dichloroethane and 15 ml of 2N hydrochloric acid until the exothermic reaction has ended. The solids are filtered off with suction, the aqueous phase is extracted using dichloromethane, the combined organic phases are dried over $Na_2SO_4$, and the solvent is evaporated in vacuo. This gives a total amount of 15.0 g of 2-methoxycarbonyl-5-iodobenzenesulfochloride, from the filtered and extracted product, of m.p. 119° C.-120° C.

2-Methoxycarbonyl-5-iodobenzenesulfonamide (Example 6 in U.S. Pat. No. 5,463,081)

Ammonia gas is passed at room temperature into 15.0 g of 2-methoxycarbonyl-5-iodobenzenesulfochloride in 100 ml of tetrahydrofuran until ammonia is no longer taken up.

The solution is evaporated in vacuo, the residue is stirred thoroughly with water, and the product is filtered off with suction. After drying of the filter residue at 70° C. in vacuo, 10.7 g of 2-methoxycarbonyl-5-iodobenzenesulfonamide are obtained as a white powder of m.p. 176° C.-177° C. Iodosulfuron-methyl (Example 9 of U.S. Pat. No. 5,463,081)

A solution of 1.7 g of 1,8-diazabicyclo[5.4.0]undec-7-ene in 10 ml of absolute acetonitrile is added dropwise at room temperature to a mixture of 3.4 g of 5-iodo-2-methoxycarbonyl benzenesulfonamide and 2.8 g of O-phenyl (4-methyl-6-methoxy-1,3,5-triazin-2-yl)-carbamate in 50 ml of absolute acetonitrile. The mixture is stirred at this temperature for 3 hours, concentrated to approx. ⅓ and poured into 200 ml of ice-water. The aqueous phase is extracted using diethyl ether, the pH is brought to 1-2 using concentrated hydrochloric acid, and the product is filtered off with suction. After drying in vacuo at 60° C., 3.3 g of iodosulfuron-methyl are obtained.

Iodosulfuron-methyl-sodium (in accordance with the disclosure of Suzhou Daxue Xuebao, Ziran Kexueban (2009), 25(1), 66-68, 94)

23 g of iodosulfuron-methyl (0.04 mol, 93%) was dissolved in 200 mL acetone completely. 4.0 g (0.05 mol) 50% NaOH solution was added dropwise. keep the reaction for 30 mins. The reaction flask was cooled down to below 0° C. at ice-water bath. The precipitate was filtered and collected. 21.0 g of iodosulfuron-methyl-sodium was obtained after drying.

Scheme 1. Synthesis of iodosulfuron-methyl-sodium

Figure 3:
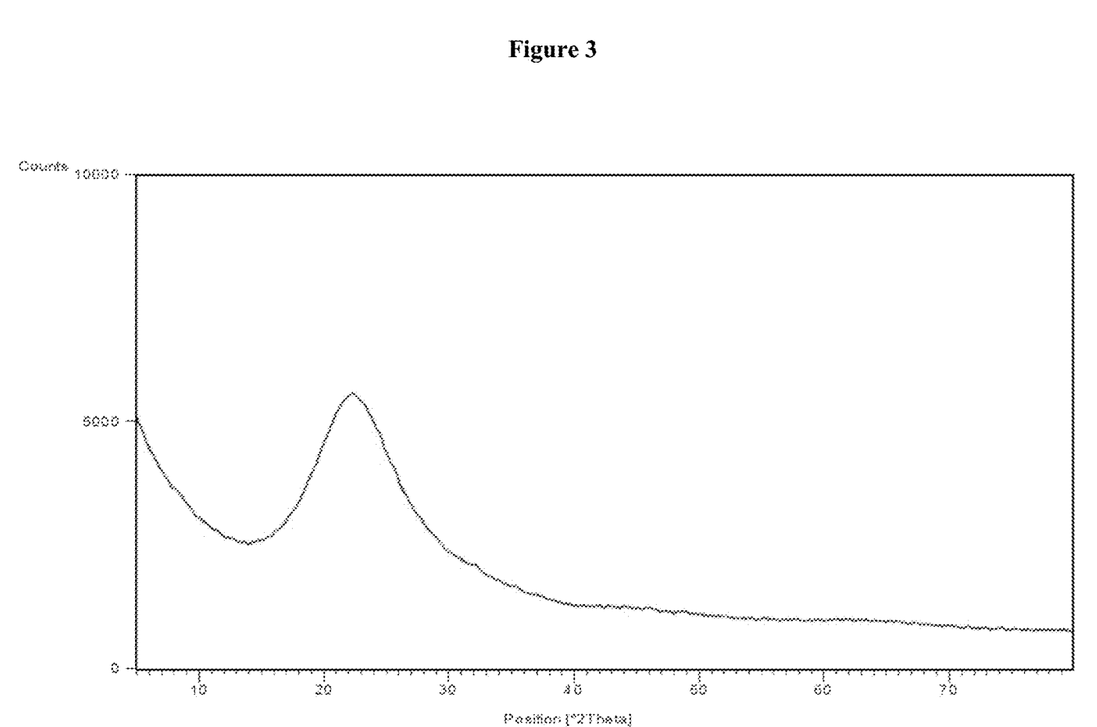
FIG. 3 is a graph showing the results of a powder X-ray diffractogram of amorphous iodosulfuron-methyl-sodium.

As shown in FIG. 3, the X-ray powder diffraction pattern of the resulting iodosulfuron-methyl-sodium products prepared above has no significant signals, which indicates the iodosulfuron-methyl-sodium product prepared in accordance with the disclosure of U.S. Pat. No. 5,463,081 and Suzhou Daxue Xuebao, Ziran Kexueban (2009), 25(1), 66-68, 94 is amorphous.

Example 2

Preparation of the Crystalline Modification I of iodosulfuron-methyl-sodium

Crystallization from Methanol 10 ml methanol was charged into the reactor to dissolve crude, amorphous iodosulfuron-methyl-sodium prepared in Example 1 under stirring. This process lasted for 2 hours under room temperature, and white solid precipitate appeared. The mixture was then cooled down to 0° C.-5° C. and maintained at this temperature for 1 hour to allow complete crystallization. After that, the mixture was centrifuged. The filter cake was washed with methanol. The resulting solid was dried under high vacuum to give crystals of pure iodosulfuron-methyl-sodium technical (Purity: 98%).

The crystals were characterized as being of the crystalline modification I of iodosulfuron-methyl-sodium using both IR spectrometry and X-ray powder diffraction.

Figure 1:
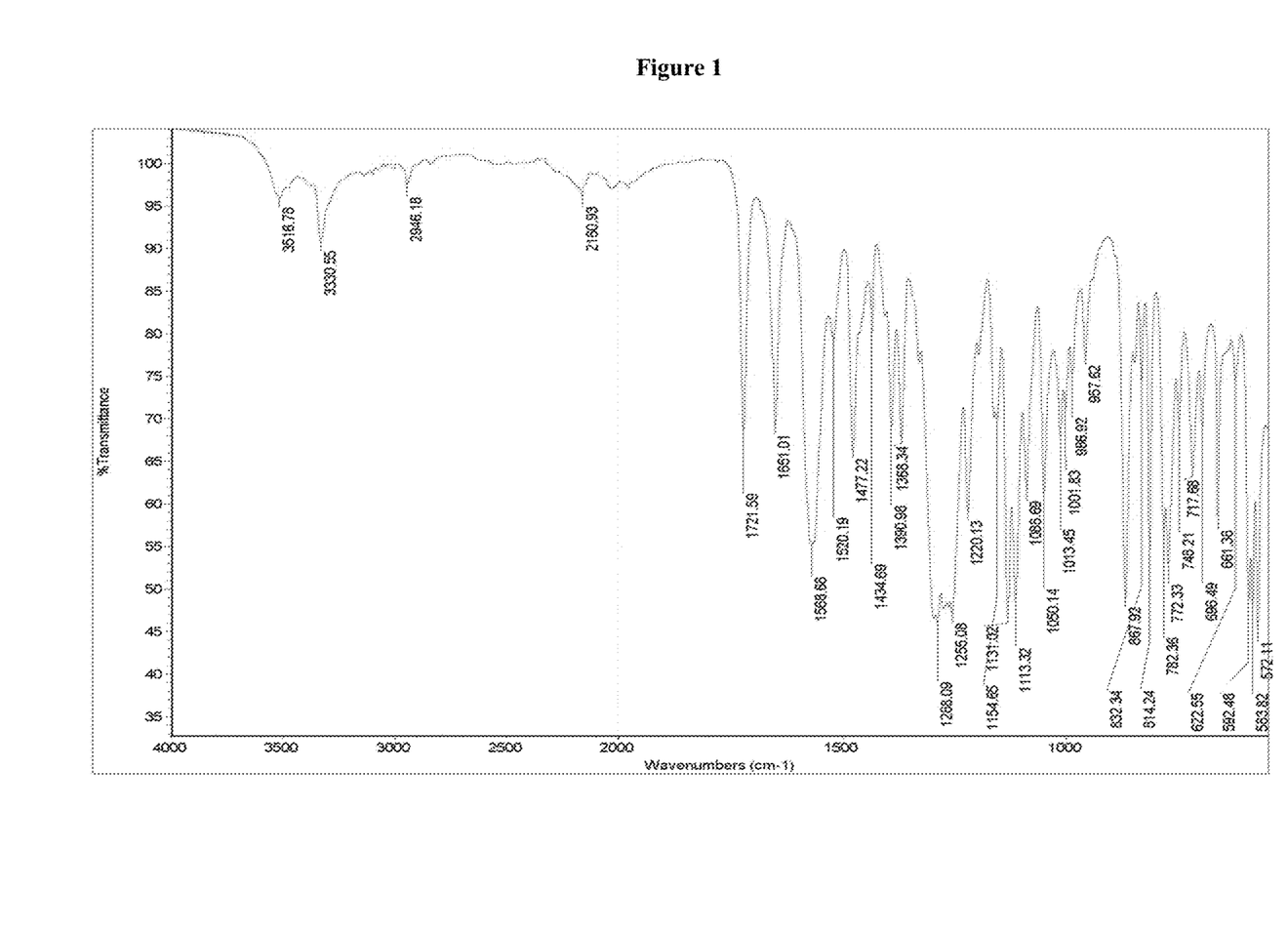
FIG. 1 is a graph showing the results of an infrared (IR) spectra of an embodiment of crystalline modification I of iodosulfuron-methyl-sodium.

The IR spectrum of the crystalline modification I of iodosulfuron-methyl-sodium is set out in FIG. 1. The IR spectrum exhibits characteristic peaks at 3516.78, 3330.55, 2946.18 and 2160.93 cm$^{-1}$.

The crystalline modification I of iodosulfuron-methyl-sodium has the X-ray powder diffractogram shown in FIG. 2 with the reflexes listed in Table 1 below.

TABLE 1

| Crystalline modification I | |
| --- | --- |
| 2 θ (°) | d (Å) |
| 11.588 ± 0.2 | 8.88 ± 0.05 |
| 14.569 ± 0.2 | 7.05 ± 0.05 |
| 18.045 ± 0.2 | 5.70 ± 0.05 |
| 19.442 ± 0.2 | 5.30 ± 0.05 |
| 20.633 ± 0.2 | 4.99 ± 0.05 |
| 23.226 ± 0.2 | 4.44 ± 0.05 |
| 26.145 ± 0.2 | 3.96 ± 0.05 |
| 27.199 ± 0.2 | 3.80 ± 0.05 |
| 27.877 ± 0.2 | 3.71 ± 0.05 |
| 29.090 ± 0.2 | 3.56 ± 0.05 |

Example 3

Preparation of the Crystalline Modification I of iodosulfuron-methyl-sodium

Crystallization from Ethanol 10 ml ethanol was charged into the reactor to dissolve crude, amorphous iodosulfuron-methyl-sodium prepared in Example 1 under stirring. This process lasted for 2 hours under room temperature, and white solid precipitate appeared. The mixture was then cooled down to 0° C.-5° C. and maintained at this temperature for 1 hour to allow complete crystallization. After that, the mixture was centrifuged. The filter cake was washed with some ethanol. The resulting solid was dried under high vacuum to give crystals of pure iodosulfuron-methyl-sodium technical (Purity: 98%).

The crystals were characterized as being the crystalline modification I of iodosulfuron-methyl-sodium using IR spectrometry and X-ray powder diffraction as described in Example 2.

Example 4

Preparation of Oil Based Suspension Concentrate (OD) Formulation

All the components listed in Table 2 below were mixed uniformly and ground with a Dyno-Mill (manufactured by Willy A. Bachofen AG) to obtain an oil based suspension concentrate.

TABLE 2

| Ingredients | Weights % | | Function |
|---|---|---|---|
| Iodosulfuron-methyl-sodium, crystalline modification I, 98% (prepared in Example 2) | 40.8 | 0 | Active compound |
| Amorphous iodosulfuron-methyl-sodium (prepared in Example 1) | 0 | 40.8 | Active compound |
| Sodium lignosulfonate (REAX ® 88B) | 22 | 22 | Dispersing agent |
| Alkylpolyvinylpyrrolidone | 20 | 20 | Thickening agent |
| Corn oil | Balance to 100% | Balance to 100% | Carrier |

Example 5

Preparation of Soluble Granules (SG)

All the components listed in Table 3 below were mixed, blended and milled in a high-speed rotary mill. Sufficient water was added to obtain an extrudable paste. The paste was extruded through a die or screen to form an extrudate. The wet extrudate was dried at 70° C. in a vacuum oven and then sifted through 0.71 mm-2 mm screens to obtain the product granules.

TABLE 3

| Ingredients | Weights % | | Function |
|---|---|---|---|
| Iodosulfuron-methyl-sodium, crystalline modification I, 98% (prepared in Example 2) | 25.51 | 0 | Active compound |
| Amorphous iodosulfuron-methyl-sodium (prepared in Example 1) | 0 | 25.51 | Active compound |
| Lignosulfonic acid, sodium salt, (REAX ® 88B) | 15 | 15 | Dispersing agent |
| Naphthalenesulfonic acid, polymer with formaldehyde, sodium salt (TAMOL ® NN 8906) | 6 | 6 | Dispersing agent |
| Sodium acetate | 4 | 4 | Filler |
| Sodium carbonate | 4 | 4 | Filler |
| Non-ionic aqueous emulsion of Polydimethylsiloxanes | 1 | 1 | Antifoaming agent |
| Mannitol | Balance to 100% | Balance to 100% | carrier |

Example 6

Preparation of Water Dispersible Granules (WG)

All the components listed in Table 4 below were mixed, blended and milled in a high-speed rotary mill. Sufficient water was added to obtain an extrudable paste. The paste was extruded through a die or screen to form an extrudate. The wet extrudate was dried at 70° C. in a vacuum oven and then sifted through 0.71 mm-2 mm screens to obtain the product granules.

TABLE 4

| Ingredients | Weights % | | Function |
|---|---|---|---|
| Iodosulfuron-methyl-sodium, crystalline modification I, 98% (prepared in Example 2) | 25.51 | 0 | Active compound |
| Amorphous iodosulfuron-methyl-sodium (prepared in Example 1) | 0 | 25.51 | Active compound |
| Alkyl naphthalene sulphonate, sodium salt (Akzo Nobel) | 2 | 2 | Wetting agent |
| Lignosulfonic acid, sodium salt, REAX ® 88B) | 15 | 15 | Dispersing agent |
| Naphthalenesulfonic acid, polymer with formaldehyde, sodium salt (TAMOL ® NN8906) | 6 | 6 | Dispersing agent |
| Sucrose | 10 | 10 | Filler |
| Non-ionic aqueous emulsion of Polydimethylsiloxanes | 1 | 1 | Antifoaming agent |
| Mannitol | Balance to 100% | Balance to 100% | Carrier |

Example 7

Stability Test

The stability of the iodosulfuron-methyl-sodium in these compositions was determined by aging samples in heated ovens having the same atmosphere therein, and then comparing the iodosulfuron-methyl-sodium content before and after the aging to determine relative percentage of hydrolysis (RPH). RPH was calculated by the following equation:

$$RPH = \frac{\left(\begin{array}{c}\text{The final weight \% of iodosulfuron-methyl-sodium} - \\ \text{The initial weight \% of iodosulfuron-methyl-sodium}\end{array}\right)}{\text{The initial weight \% of iodosulfuron-methyl-sodium}} \times 100\%$$

Iodosulfuron-methyl-sodium content was determined by assaying the compositions with high-pressure liquid chromatography (HPLC) using reverse phase columns and eluants.

Samples prepared in Examples 4, 5 and 6 were stored at 54° C. for 1 week. The procedures are followed according to CIPAC MT 46.3. The concentration of iodosulfuron-methyl-sodium was measured at the end of each storage time by HPLC. The results are listed in Table 5.

TABLE 5

| Sample | Compound | Weight (%) of iodosulfuron-methyl-sodium | RPH % |
|---|---|---|---|
| Example 4 | Iodosulfuron-methyl-sodium, crystalline modification I | 40 | 0 |
| | Amorphous iodosulfuron-methyl-sodium | 40 | 49 |
| Example 5 | Iodosulfuron-methyl-sodium, crystalline modification I | 25 | 0 |
| | Amorphous iodosulfuron-methyl-sodium | 25 | 42 |
| Example 6 | Iodosulfuron-methyl-sodium, crystalline modification I, | 25 | 0 |
| | Amorphous iodosulfuron-methyl-sodium | 25 | 40 |

The invention claimed is:

1. A crystalline modification I of iodosulfuron-methyl-sodium obtained by (i) dissolving amorphous iodosulfuron-methyl-sodium in a solvent to obtain a solution, wherein the solvent is methanol, ethanol, or a mixture thereof, (ii) mixing the solution at room temperature to obtain a solid precipitate, (iii) cooling the solution including the solid precipitate, (iv) centrifuging the cooled solution to obtain filtered crystals, (v) washing the filtered crystals with the alcohol, and (vi) drying the washed crystals under vacuum, wherein the obtained crystalline modification I of iodosulfuron-methyl-sodium exhibiting each of the following reflexes in an X-ray powder diffractogram recorded using Cu—Kα radiation at 25° C.:

$2\theta=11.558\pm0.2$ (1)

$2\theta=14.569\pm0.2$ (2)

$2\theta=18.045\pm0.2$ (3)

$2\theta=19.442\pm0.2$ (4)

$2\theta=20.633\pm0.2$ (5)

$2\theta=23.226\pm0.2$ (6)

$2\theta=26.145\pm0.2$ (7)

$2\theta=27.199\pm0.2$ (8)

$2\theta=27.877\pm0.2$ (9)

$2\theta=29.090\pm0.2$ (10).

2. The crystalline modification I of iodosulfuron-methyl-sodium according to claim 1, exhibiting IR spectrum with the characteristic bands at 3516.78, 3330.55, 2946.18 and 2160.93 cm$^{-1}$.

3. A composition comprising the crystalline modification I of iodosulfuron-methyl-sodium according to claim 1 and at least one herbicidally acceptable auxiliary.

4. The composition according to claim 3, wherein the composition is in the form of a suspension concentrates (SC), an oil-based suspension concentrates (OD), water-soluble granules (SG), a dispersible concentrate (DC), an emulsifiable concentrates (EC), an emulsion seed dressing, a suspension seed dressing, granules (GR), microgranules (MG), a suspoemulsion (SE) or water-dispersible granules (WG).

5. The composition according to claim 4, wherein the composition is in the form of an oil-based suspension concentrate (OD).

6. The composition according to claim 4, wherein the composition is in the form of water-dispersible granules (WG).

7. The composition according to claim 4, wherein the composition is in the form of water-soluble granules (SG).

8. The composition according to claim 3, wherein the auxiliary is selected from one or more of a diluent, a wetting agent, a dispersant, and a thickening agent.

9. The composition according to claim 3, which comprises crystalline modification I of iodosulfuron-methyl-sodium in an amount of less than 75% by weight.

10. A method of controlling unwanted plant growth comprising applying to a plant, plant part, or locus thereof a herbicidally effective amount of crystalline modification I of iodosulfuron-methyl-sodium according to claim 1.

* * * * *